(12) United States Patent
Kim et al.

(10) Patent No.: US 11,413,019 B2
(45) Date of Patent: Aug. 16, 2022

(54) METHOD AND APPARATUS FOR DISPLAYING ULTRASOUND IMAGE OF TARGET OBJECT

(71) Applicant: SAMSUNG MEDISON CO., LTD., Hongcheon-gun (KR)

(72) Inventors: Han-jun Kim, Hongcheon-gun (KR); Sung-yoon Kim, Hongcheon-gun (KR); Jong-sik Kim, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 236 days.

(21) Appl. No.: 16/476,912

(22) PCT Filed: Apr. 17, 2017

(86) PCT No.: PCT/KR2017/004096
§ 371 (c)(1),
(2) Date: Jul. 10, 2019

(87) PCT Pub. No.: WO2018/131754
PCT Pub. Date: Jul. 19, 2018

(65) Prior Publication Data
US 2021/0128113 A1    May 6, 2021

(30) Foreign Application Priority Data
Jan. 10, 2017    (KR) .................. 10-2017-0003401

(51) Int. Cl.
*A61B 8/00*    (2006.01)
*A61B 8/06*    (2006.01)
(Continued)

(52) U.S. Cl.
CPC ................ *A61B 8/467* (2013.01); *A61B 8/06* (2013.01); *A61B 8/085* (2013.01); *A61B 8/0891* (2013.01);
(Continued)

(58) Field of Classification Search
CPC .......... A61B 8/085; A61B 8/06; A61B 8/466; A61B 8/5246; A61B 8/0891; G06T 19/20
See application file for complete search history.

(56) References Cited

U.S. PATENT DOCUMENTS 7,742,629 B2    6/2010   Zarkh et al.
8,315,963 B2    11/2012  Weimker et al.
(Continued)

FOREIGN PATENT DOCUMENTS

JP    2009-539540 A    11/2009
JP    2012-187342 A    10/2012
(Continued)

OTHER PUBLICATIONS

Written Opinion (PCT/ISA/237) issued by the International Searching Authority in corresponding International Application No. PCT/KR2017/004096, dated Aug. 23, 2017.
(Continued)

*Primary Examiner* — Amanda Lauritzen Moher
*Assistant Examiner* — Sean V Blinder
(74) *Attorney, Agent, or Firm* — Sughrue Mion, PLLC

(57) ABSTRACT

Provided is an ultrasound imaging apparatus comprising: an image processing unit for connecting relevant blood flows and classifying the same into a plurality of blood flow trees on the basis of information on blood flow direction and blood flow velocity obtained from morphological information of a target object and three-dimensional blood flow data; a user input unit for receiving a user input which selects a blood flow tree, in which a target blood flow is included, from among the plurality of blood flow trees; and a display unit for displaying the selected blood flow tree on a three-dimensional rendering image on the basis of the user input.

15 Claims, 16 Drawing Sheets

(51) Int. Cl.
*A61B 8/08* (2006.01)
*G06T 19/00* (2011.01)

(52) U.S. Cl.
CPC .............. *A61B 8/461* (2013.01); *A61B 8/463* (2013.01); *A61B 8/466* (2013.01); *A61B 8/5246* (2013.01); *G06T 19/00* (2013.01); *G06T 2200/24* (2013.01); *G06T 2207/10132* (2013.01); *G06T 2207/10136* (2013.01)

(56) References Cited

U.S. PATENT DOCUMENTS

| | | | |
|---|---|---|---|
| 9,996,918 | B2 | 6/2018 | Kim et al. |
| 10,327,847 | B2 | 6/2019 | Taylor |
| 10,842,568 | B2 * | 11/2020 | Hart ..................... A61B 5/0263 |
| 2002/0151795 | A1 * | 10/2002 | Palti ......................... A61B 8/06 600/454 |
| 2014/0327667 | A1 | 11/2014 | Kim et al. |
| 2014/0343431 | A1 | 11/2014 | Vajinepalli et al. |
| 2017/0053092 | A1 * | 2/2017 | Taylor .................. A61B 5/0044 |

FOREIGN PATENT DOCUMENTS

| | | |
|---|---|---|
| JP | 5129480 B2 | 1/2013 |
| JP | 2015-66311 A | 4/2015 |
| KR | 10-1442728 B1 | 9/2014 |
| KR | 10-2015-0070446 A | 6/2015 |
| WO | 2010/014201 A2 | 2/2010 |
| WO | 2012/021307 A2 | 2/2012 |
| WO | 2016/170076 A1 | 10/2016 |

OTHER PUBLICATIONS

International Search Report (PCT/ISA/210), issued by International Searching Authority in corresponding International Application No. PCT/KR2017/004096, dated Aug. 23, 2017.

* cited by examiner

METHOD AND APPARATUS FOR DISPLAYING ULTRASOUND IMAGE OF TARGET OBJECT

TECHNICAL FIELD

The disclosure relates to a method and an apparatus for displaying an ultrasound image of a target object, and more particularly, to a method and an apparatus for visualizing only a blood stream of interest to be observed by a user among blood streams included in the target object.

BACKGROUND ART

An ultrasound imaging apparatus irradiates an ultrasound signal generated from a transducer of a probe to a target object and receives information of a signal reflected from the target object to obtain at least one image of a site (for example, a soft tissue or a blood stream) inside the target object.

A method of setting a region of interest in an ultrasound image of a target object and displaying a region of interest (ROI) is known. The currently known methods of setting the ROI involve an operation in conjunction with a blood stream as well as other tissue data of a target object. Also, due to the characteristics of the blood stream having various three-dimensional distributions, there is a technical limitation in accurately visualizing and displaying only a blood stream of interest in the target object using the currently known methods of setting the ROI.

DESCRIPTION OF EMBODIMENTS

Technical Problem

Provided are a method and an apparatus for displaying only a blood stream of interest to be observed by a user among blood streams included in an ultrasound image of a target object.

Advantageous Effects of Disclosure

According to an embodiment of the disclosure, an ultrasound imaging apparatus and an operation method thereof may classify blood streams in a target body into a plurality of blood stream trees by grouping relevant blood streams based on three-dimensional ultrasound volume data and blood stream data of the target object, and visualizing and displaying only a blood stream to be observed among the classified plurality of blood streams, thereby reliably removing an unnecessary noise signal and allowing a user to clearly observe only a blood stream of interest.

BRIEF DESCRIPTION OF DRAWINGS

The above and other aspects, features, and advantages of certain embodiments of the disclosure will be more apparent from the following description taken in conjunction with the accompanying drawings, in which.

BEST MODE

Figure 1:
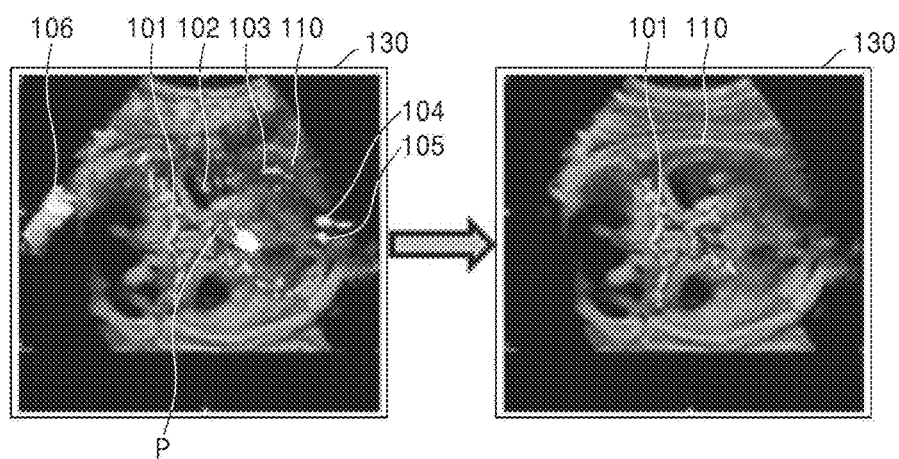
FIG. 1 is a conceptual diagram for explaining a method, performed by an ultrasound imaging apparatus, of displaying an ultrasound image of a target object, according to an embodiment of the disclosure.

In accordance with an aspect of the disclosure, an ultrasound imaging apparatus for displaying an ultrasound image of a target object includes an image processor configured to: obtain three-dimensional (3D) ultrasound volume data relating to the target object and 3D blood stream data related to a blood stream in the target object, connect relevant blood streams based on shape information of the target object obtained from the 3D ultrasound volume data and blood stream direction and blood stream velocity information obtained from the 3D blood stream data, and classify the relevant blood streams into a plurality of blood stream trees; a user inputter configured to receive a user input for selecting a first blood stream tree including a blood stream of interest from among the plurality of blood stream trees; and a display displaying, on a 3D rendering image, the first blood stream tree selected based on the user input.

In accordance with another aspect of the disclosure, a method of displaying an ultrasound image of a target object includes obtaining three-dimensional (3D) ultrasound volume data relating to the target object and 3D blood stream data related to a blood stream in the target object; connecting relevant blood streams based on shape information of the target object obtained from the 3D ultrasound volume data and blood stream direction and blood stream velocity information obtained from the 3D blood stream data, and classifying the relevant blood streams into a plurality of blood stream trees; receiving a user input for selecting a first blood stream tree including a blood stream of interest from among the plurality of blood stream trees; and displaying, on a 3D rendering image, the first blood stream tree selected based on the user input.

In accordance with another aspect of the disclosure, a computer-readable recording medium having recorded thereon a program for executing the method in a computer is provided.

Mode of Disclosure

This application is based on and claims priority to Korean Patent Application No. 10-2017-0003401, filed on Jan. 10, 2017, in the Korean Intellectual Property Office.

The present specification describes principles of the disclosure and sets forth embodiments thereof to clarify the scope of the disclosure and to allow those of ordinary skill in the art to implement the embodiments of the disclosure. The present embodiments of the disclosure may have different forms and should not be construed as being limited to the descriptions set forth herein.

Like reference numerals refer to like elements throughout. The present specification does not describe all components in the embodiments of the disclosure, and common knowledge in the art or the same descriptions of the embodiments of the disclosure will be omitted below. The term 'part' or 'portion' used herein may be implemented using hardware or software, and according to embodiments of the disclosure, a plurality of 'parts' or 'portions' may be formed as a single unit or element, or one 'part' or 'portion' may include a plurality of units or elements. Hereinafter, the operating principles and embodiments of the disclosure will be described in detail with reference to the accompanying drawings.

In the present specification, an image may include any medical image obtained by various medical imaging apparatuses such as a magnetic resonance imaging (MRI) apparatus, a computed tomography (CT) apparatus, an ultrasound imaging apparatus, or an X-ray apparatus.

Also, in the present specification, an 'object', which is a thing to be imaged, may include a human, an animal, or a part thereof. For example, an object may include a part of a human, that is, an organ or a tissue, or a phantom.

Further, in the present specification, a "user" may be, but is not limited to, a medical expert, such as a medical doctor, a nurse, a medical laboratory technologist, or a technician who repairs a medical apparatus.

Further, in the present specification, a 'blood stream of interest' means a blood stream to be observed by a user (a doctor or an ultrasound imaging operator) in at least one blood stream contained in an object.

Also, in the present specification, expressions such as "first", "second", or "1-1th" are exemplary terms for designating different components, entities, data units, images, pixels or patches. Therefore, the expressions such as "first", "second", or "1-1th" do not indicate order between the components or indicate priority.

Reference will now be made in detail to embodiments, examples of which are illustrated in the accompanying drawings. In the following description, well-known functions or constructions are not described in detail so as not to obscure the embodiments with unnecessary detail.

FIG. 1 is a conceptual diagram for explaining a method, performed by an ultrasound imaging apparatus, of displaying a three-dimensional (3D) ultrasound rendering image 100 of a target object according to an embodiment of the disclosure.

Referring to FIG. 1, a display 130 of the ultrasound imaging apparatus may display the 3D ultrasound rendering image 100 of the target object. The 3D ultrasound rendering image 100 may be an image of 3D ultrasound volume data obtained by receiving an ultrasound echo signal reflected from the target object. The 3D ultrasound rendering image 100 may include images of a plurality of blood stream trees 101 to 106 configured as blood streams in the target object and a tissue 110.

The ultrasound imaging apparatus may transmit an ultrasound signal to the target object and receive the ultrasound signal reflected from the target object to obtain the 3D ultrasound volume data and blood stream data of the target object. The obtained blood stream data may include information about blood stream directions and blood stream velocities of the blood streams in the target object. In an embodiment, the ultrasound imaging apparatus may connect and classify relevant blood streams into the plurality of blood stream trees 101 to 106 based on a shape of the tissue 110 of the target object and the blood stream directions and blood stream velocities of the blood streams.

The display 130 may display the plurality of classified blood stream trees 101 to 106 on the 3D ultrasound rendering image 100. The ultrasound imaging apparatus may receive a user input P for selecting the first blood stream tree 101 including a blood stream of interest to be observed among the plurality of blood stream trees 101 to 106 included in the 3D ultrasound rendering image 100.

The ultrasound imaging apparatus may visualize and display only the selected first blood stream tree 101 based on the received user input P on 3D volume data.

The blood stream data, such as the blood stream directions and blood stream velocities in an ultrasound image, may include artifact noise due to a motor swing of an ultrasound motor or a movement of a tissue in the target object. Conventionally, in order to reduce the artifact noise of the blood stream data on the ultrasound image, a technique (a low threshold method or a power threshold method) of adjusting a threshold value of intensity of a signal, a technique (a balance method) of displaying only a darkly displayed region as a blood stream using B mode image data, etc. are known in the field of ultrasound image processing. However, these techniques have a disadvantage in that the artifact noise of the blood stream data may not be completely removed. Further, because the conventional method of setting a 3D region of interest (ROI) operates in conjunction with tissue data of the target object, it is difficult to split and display only the blood stream information due to the characteristics of the blood stream having 3D various distributions.

The ultrasound imaging apparatus according to an embodiment of the disclosure may classify blood streams in the target body into the plurality of blood stream trees 101 to 106 by grouping relevant blood streams based on the 3D ultrasound volume data and the blood stream data of the target object, and visualize and display only the first blood stream tree 101 based on the user input P for selecting a blood stream tree (the first blood stream tree 101) to be observed among the classified plurality of blood stream trees 101 to 106. Therefore, an unnecessary noise signal may be reliably removed and the user may clearly observe only the blood stream of interest.

Figure 2:
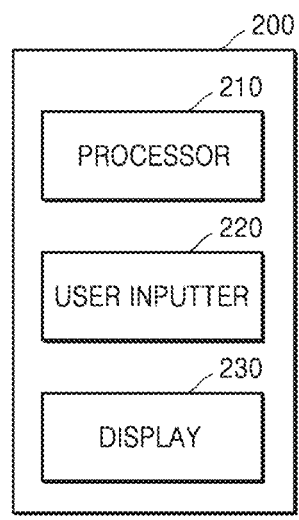
FIG. 2 is a block diagram showing a structure of an ultrasound imaging apparatus according to an embodiment of the disclosure.

FIG. 2 is a block diagram showing a structure of an ultrasound imaging apparatus 200 according to an embodiment of the disclosure. In an embodiment, the ultrasound imaging apparatus 200 may be implemented in a portable type as well as a cart type. Examples of a portable ultrasound diagnosis apparatuses include, but are not limited to, a PACS viewer, a smart phone, a laptop computer, a PDA, a tablet PC, and the like.

Referring to FIG. 2, the ultrasound imaging apparatus 200 may include an image processor 210, a user inputter 220, and a display 230. However, the ultrasound imaging apparatus 200 does not only include the illustrated components, but may further include other components. In an embodiment, the ultrasound imaging apparatus 200 may further include an ultrasound probe for transmitting an ultrasound wave to a target object and receiving an ultrasound echo signal reflected from the target object, and a data generator for obtaining ultrasound data from the received ultrasound echo signal.

The image processor 210 may receive ultrasound data from the data generator. In an embodiment, the ultrasound data may include 3D ultrasound volume data and blood stream data. The 3D ultrasound volume data may include B mode image data about a tissue in a target object. The blood stream data may include Doppler data including information about a blood stream direction and a blood stream velocity in the target object.

The image processor 210 may connect relevant blood streams based on shape information of the target body obtained from the 3D ultrasound volume data and the information about the blood stream direction and the blood stream velocity obtained from the blood stream data and may classify the blood streams in the target body into a plurality of blood stream trees. Here, the relevant blood stream may mean at least one of blood streams that are shapely and structurally connected to each other among the blood streams in the object, blood streams of the same blood stream direction, blood streams having a similar blood stream average velocity within a predetermined range, and a combination of these.

In a pre-processing operation, the image processor 210 may remove noise of data and improve connectivity using a known edge-preserving smoothing technique, etc., and analyze the information about the blood stream direction and the blood stream average velocity through various statistical approaches such as a histogram analysis technique of a data local region.

After pre-processing and analysis of the blood stream data described above, the image processor 210 may classify the relevant blood streams into the plurality of blood stream trees using segmentation techniques such as connected component labeling or K-clustering, etc. The techniques used by the image processor 210 are well known in the art of ultrasound image processing, and thus a detailed description thereof is omitted.

When receiving a user input for selecting a specific region in the 3D volume data, the image processor 210 may calculate a 3D location coordinate value (X, Y, Z) of the region selected by the user input. The image processor 210 may select a blood stream located in the calculated 3D location coordinate value (X, Y, Z) among the plurality of classified blood stream trees, and select a blood stream tree including the selected blood stream.

The user inputter 220 may receive a user input for selecting a blood stream tree including a blood stream to be observed among the plurality of blood stream trees in the 3D volume data of the target object. In an embodiment, the user inputter 220 may include, but is not limited to, a hardware configuration such as a keypad, a mouse, a trackball, a touch pad, a touch screen, a jog switch, etc.

In an embodiment, the user inputter 220 may receive a first user input for connecting a first blood stream tree and a second blood stream tree to each other. Also, the user inputter 220 may receive a second user input for separating the previously selected first blood stream tree into two or more blood streams. Also, the user inputter 220 may receive a third user input for removing a blood stream tree of no interest when a plurality of blood stream trees are selected.

In an embodiment, the user inputter 220 may receive user input for mapping different colors to respective blood streams included in the previously selected first blood stream tree. For example, the user inputter 220 may receive a user input for mapping a red color to the arteries in the first blood stream tree, and a blue color to the veins.

The display 230 may display a 3D ultrasound rendering image of the target object. The display 230 may be implemented as a physical device including at least one of, for example, a CRT display, an LCD display, a PDP display, an OLED display, an FED display, an LED display, a VFD display, a digital light processing (DLP) display, a flat panel display, a 3D display, and a transparent display, but is not limited thereto. In an embodiment, the display 230 may be configured as a touch screen including a touch interface. When the display 230 is configured as the touch screen, the display 230 may be integrated with the user inputter 220 as one component. In an embodiment, the ultrasound imaging apparatus 200 may include two or more displays 230, according to an implementation.

In an embodiment, the display 230 may display the selected blood stream tree on the 3D ultrasound rendering image based on the user input received in the user inputter 220. In an embodiment, the display 230 may display the colors mapped to the arteries and the veins in the previously selected blood stream tree on the 3D volume data.

The display 230 may output not only the 3D ultrasound rendering image but also various information processed in the ultrasound imaging apparatus 200 in the form of a graphic user interface (GUI).

Figure 3:
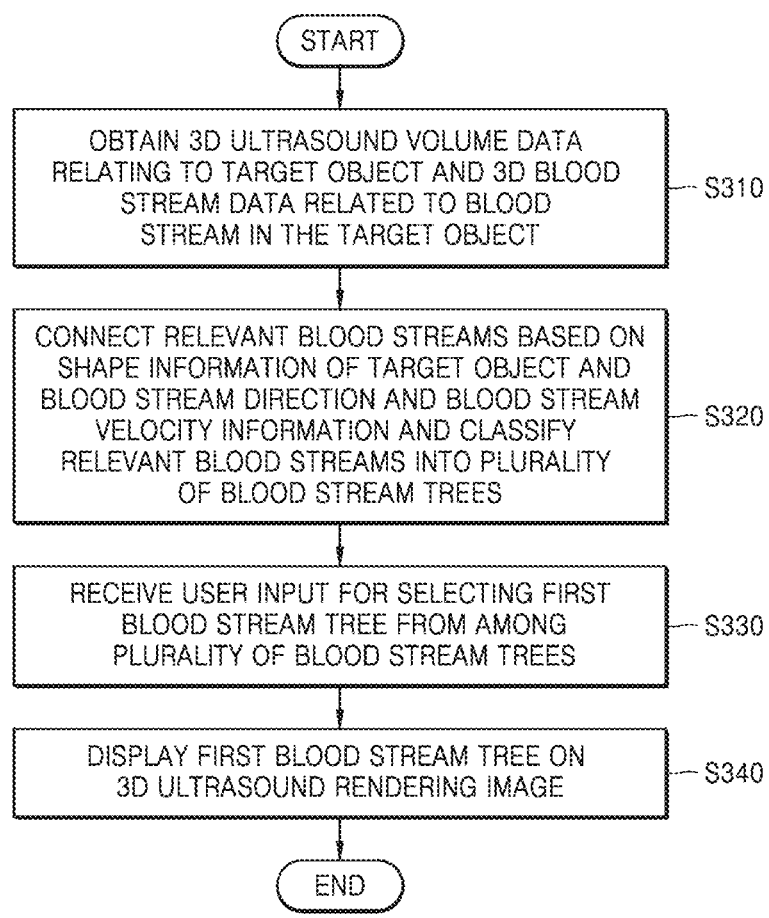
FIG. 3 is a flowchart illustrating a method, performed by an ultrasound imaging apparatus, of displaying a blood stream of interest included in an ultrasound image of a target object, according to an embodiment of the disclosure.

FIG. 3 is a flowchart illustrating a method, performed by an ultrasound imaging apparatus, of displaying a blood stream of interest included in an ultrasound image of a target object according to an embodiment of the disclosure.

In operation S310, the ultrasound imaging apparatus may obtain 3D ultrasound volume data of the target object and 3D blood stream data of a blood stream. The 3D ultrasound volume data may include B mode image data relating to a tissue in the target object, and the blood stream data may include Doppler data including information about a blood stream direction and a blood stream velocity in the target object.

In operation S320, the ultrasound imaging apparatus may connect relevant blood streams based on shape information of the target body and information about the blood stream direction and the blood stream velocity and may classify the blood streams into a plurality of blood stream trees. In an embodiment, the ultrasound imaging apparatus may obtain shape information of tissues and blood streams in the target object in the B mode image data, and obtain information about the blood stream direction and the blood stream velocity from Doppler data. In an embodiment, the ultrasound imaging apparatus may classify the relevant blood streams into the plurality of blood stream trees using segmentation techniques such as connected component labeling or K-clustering, etc.

In operation S330, the ultrasound imaging apparatus receives a user input for selecting a first blood stream tree among the plurality of blood stream trees. The ultrasound imaging apparatus may receive the user input for selecting the first blood stream tree including the blood stream of interest to be observed by a user among the plurality of blood stream trees displayed on a 3D ultrasound rendering image. In an embodiment, the ultrasound imaging apparatus may receive at least one user input of a click input using a mouse, a drag input using a trackball, a touch input to touch a touch screen, and a combination of these.

In operation S340, the ultrasound imaging apparatus displays the first blood stream tree on the 3D volume data. In an embodiment, the ultrasound imaging apparatus may not display the remaining blood stream trees except for the first blood stream tree among the plurality of blood stream trees displayed on the 3D ultrasound rendering image of the target object in operation S330. By displaying only the blood stream of interest selected by the user, the visibility of the blood stream may be increased and information unnecessary for diagnosis may be excluded in advance.

Figure 4A:
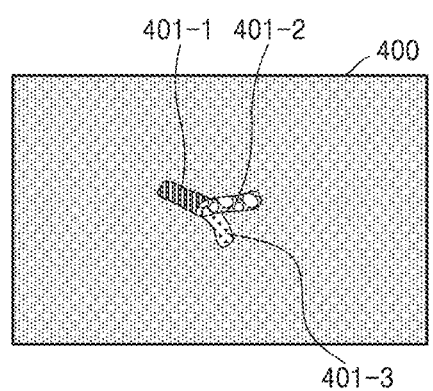
FIGS. 4A to 4C are diagrams for explaining a method, performed by an ultrasound imaging apparatus, of displaying a blood stream of interest in an ultrasound image, according to an embodiment of the disclosure.
Figure 4B:
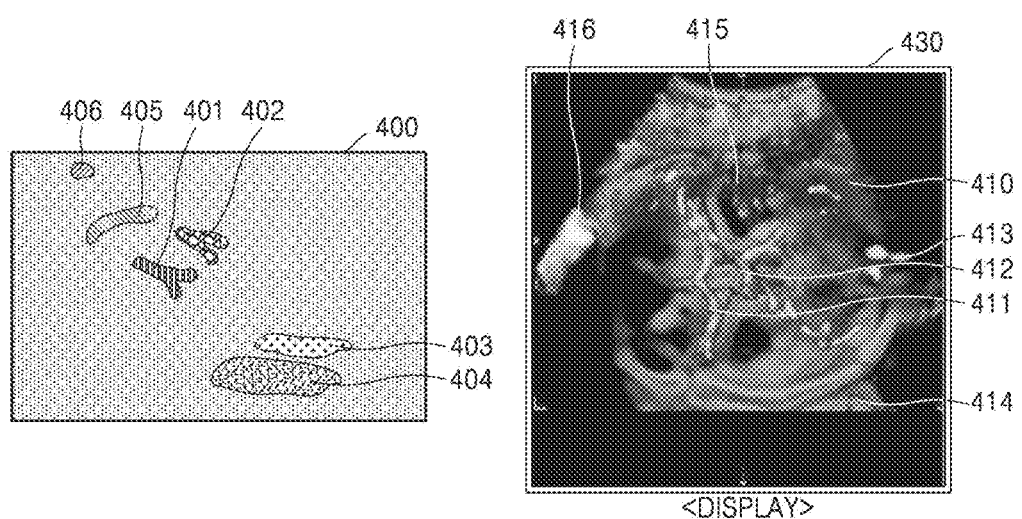
Figure 4C:
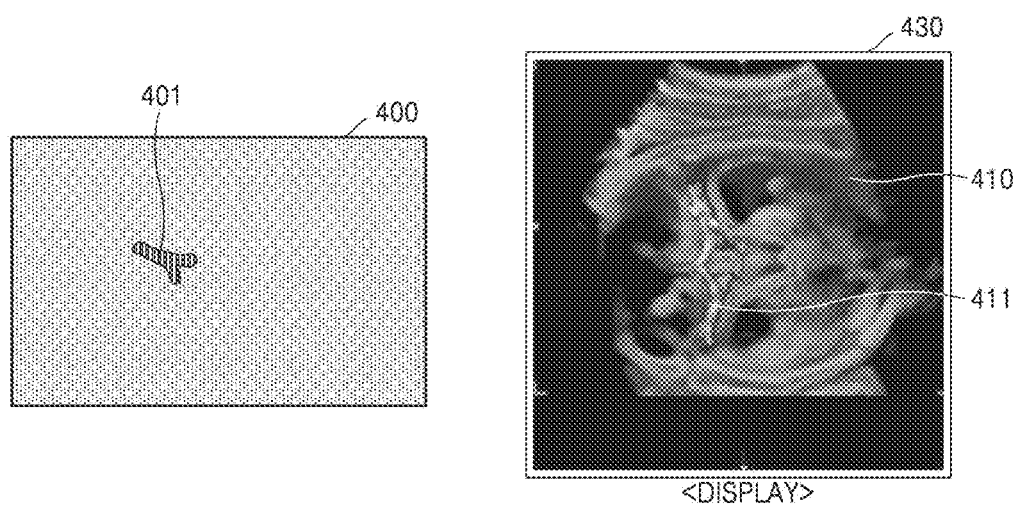

FIGS. 4A to 4C are diagrams for explaining a method, performed by an ultrasound imaging apparatus, of displaying a blood stream of interest in an ultrasound image on a display 430 according to an embodiment of the disclosure. In FIGS. 4A to 4C, 3D ultrasound volume data 400 in FIGS. 4A to 4C may be frame data of one of 3D blood stream Doppler data obtained by the image processor 210 (see FIG. 2).

Referring to FIG. 4A, the 3D ultrasound volume data 400 may include a first blood stream 401-1 to a third blood stream 401-3. The image processor 210 may detect the first blood stream 401-1 to the third blood stream 401-3 included in the 3D ultrasound volume data 400 of the target object. In an embodiment, the image processor 210 may detect a boundary line of each of the first blood stream 401-1 to the third blood stream 401-3 from the 3D ultrasound volume data 400 using a technique known in the art of ultrasound image processing, such as an edge-preserving smoothing technique or a connected component labeling technique, etc. and analyze the connectivity.

The image processor 210 may classify the first blood stream 401-1 to the third blood stream 401-3 in the 3D ultrasound volume data 400 into one blood stream tree based on shape characteristic information such as structural similarity, distance proximity, etc. and information obtained from Doppler data such as a blood stream direction, a blood stream average velocity, etc.

In FIG. 4B, the image processor 210 (see FIG. 2) may classify a plurality of blood streams in the target object into a plurality of blood stream trees 401 to 406 by connecting relevant blood streams. The first blood stream 401-1 to the third blood stream 401-3 shown in FIG. 4A may be classified into the first blood stream tree 401. In an embodiment, the image processor 210 may classify the relevant blood streams into the plurality of blood stream trees 401 to 406 using a technique known in the field of ultrasound image processing such as K-Clustering or labeling technology after a pre-processing and blood stream analysis process described above in FIG. 4A.

The display 430 may display a plurality of blood stream trees 411 to 416 on a 3D ultrasound rendering image 410 related to the target object. The first blood stream tree 411 to the sixth blood stream tree 416 displayed on the display 430 may mean the same as those of the first blood stream tree 401 to the sixth blood stream tree 406 included in the 3D ultrasound volume data 400.

Referring to FIG. 4C, the ultrasound imaging apparatus may select and display only the first blood stream tree 411 according to a received user input among the plurality of blood stream trees 411 to 416 (see FIG. 4B) displayed on the display 430. In an embodiment, when a user input for selecting a specific region on the 3D ultrasound rendering image 410 of the target object displayed on the display 430 is received, the image processor 210 (see FIG. 2) may calculate a 3D location coordinate value of the received specific region and select the first blood stream tree 411 located at the calculated 3D location coordinate value.

When a user input for selecting the first blood stream tree 411 is received, the display 430 may display only the first blood stream tree 411 on the 3D ultrasound rendering image 410. That is, the second blood stream tree 412 through the sixth blood stream tree 416 (see FIG. 4B) may no longer be displayed on the display 430.

Figure 5:
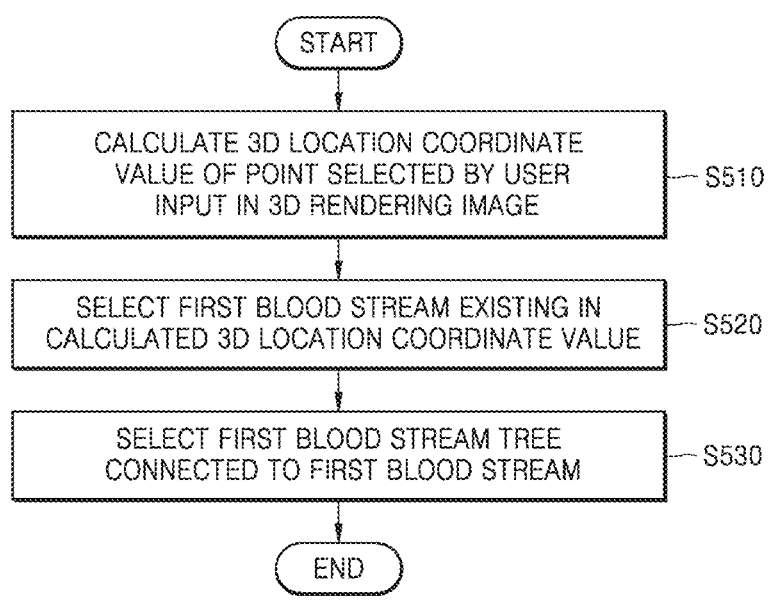
FIG. 5 is a flowchart illustrating a method, performed by an ultrasound imaging apparatus, of selecting a blood stream of interest based on a user input, according to an embodiment of the disclosure.

FIG. 5 is a flowchart illustrating a method, performed by an ultrasound imaging apparatus, of selecting a blood stream of interest based on a user input according to an embodiment of the disclosure.

In operation S510, the ultrasound imaging apparatus calculates a 3D location coordinate value of a point selected by the user input in a 3D ultrasound rendering image. In an embodiment, a display of the ultrasound imaging apparatus may display a 3D ultrasound rendering image including blood stream data related to blood streams in a target object. The ultrasound imaging apparatus may pre-process 3D ultrasound volume data and analyze blood stream data to classify and display relevant blood streams in the target object into a plurality of blood stream trees. The ultrasound imaging apparatus may receive the user input for selecting a blood stream tree of interest to be observed among the plurality of blood stream trees. In an embodiment, the ultrasound imaging apparatus may calculate the 3D location coordinate value (X, Y, Z) of the selected point based on the user input received by a user. X and Y axes of the selected point may be calculated by recognizing a location of a two-dimensional (2D) coordinate value of the user input and by calculating depth information according to an accumulated value of light of the 3D ultrasound volume data of Z axis.

In operation S520, the ultrasound imaging apparatus selects a first blood stream existing in the calculated 3D location coordinate value. In an embodiment, the ultrasound imaging apparatus may select the first blood stream located at the calculated 3D location coordinate value (X, Y, Z) among the plurality of blood streams in the 3D ultrasound rendering image.

In operation S530, the ultrasound imaging apparatus selects a first blood stream tree that is a blood stream tree connected to the first blood stream. In an embodiment, the ultrasound imaging apparatus may classify relevant blood streams into a plurality of blood stream trees by using a K-Clustering or labeling technique after pre-processing the 3D ultrasound volume data and analyzing the blood stream data in operation S510. The ultrasound imaging apparatus may select a first blood stream tree including the first blood stream among the classified plurality of blood stream trees.

In an embodiment, the ultrasound imaging apparatus may visualize and display only the first blood stream selected based on the user input among the plurality of blood stream trees on the 3D ultrasound rendering image.

Figure 6A:
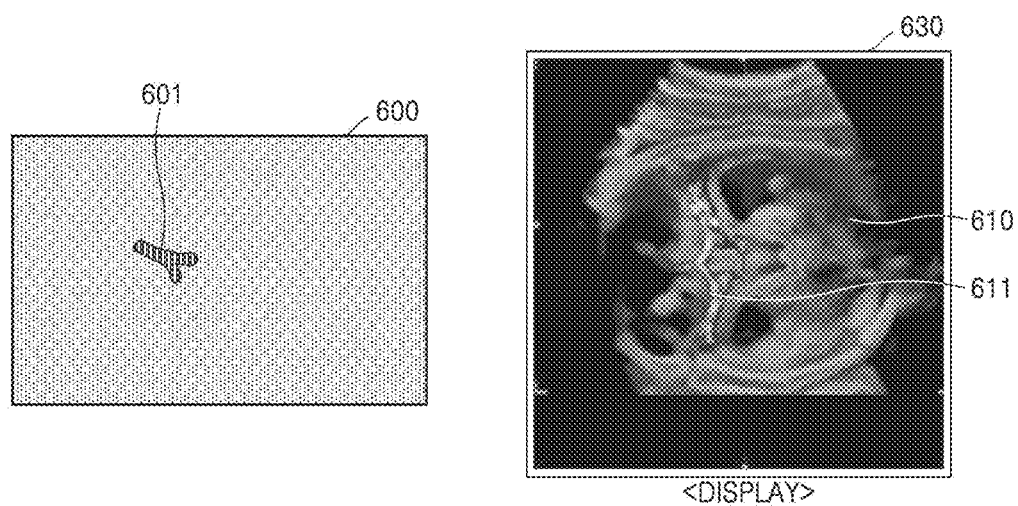
FIGS. 6A through 6C are diagrams illustrating a method, performed by an ultrasound imaging apparatus, of displaying a blood stream of interest in an ultrasound image, according to an embodiment of the disclosure.
Figure 6B:
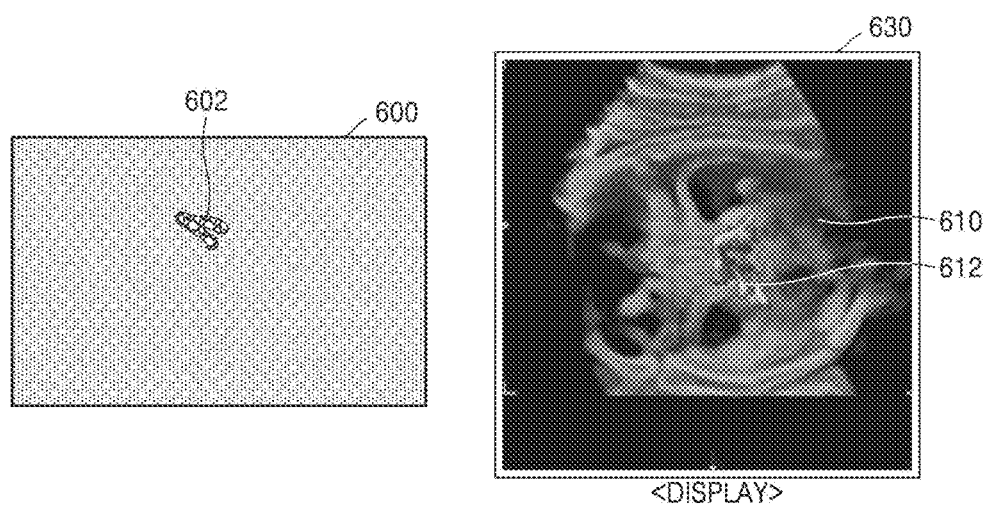
Figure 6C:
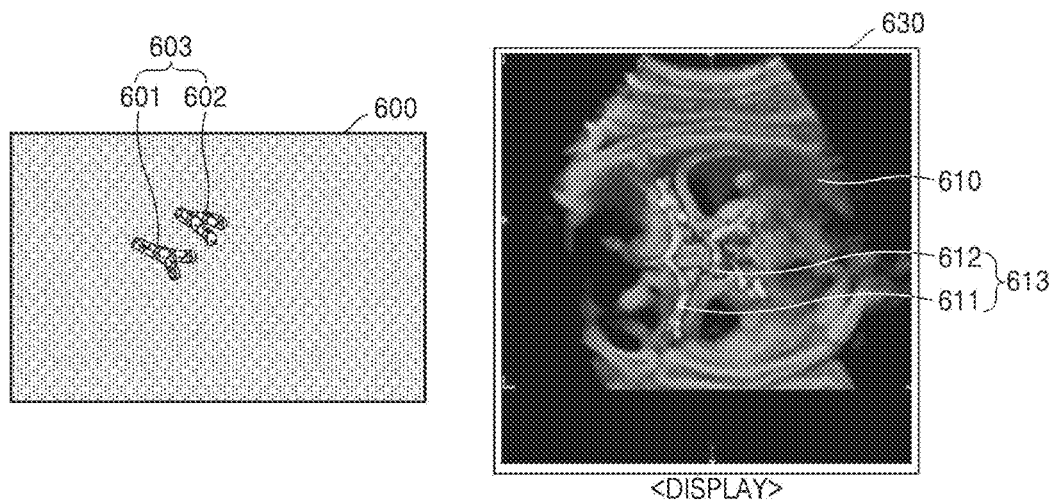

FIGS. 6A through 6C are diagrams illustrating a method, performed by an ultrasound imaging apparatus, of displaying a blood stream of interest in an ultrasound image on a display 630 according to an embodiment of the disclosure.

In FIGS. 6A through 6C, 3D ultrasound volume data 600 may be data of one sheet of frame among 3D blood stream Doppler data obtained by the image processor (210, see FIG. 2).

Referring to FIG. 6A, the ultrasound imaging apparatus may receive a user input for selecting a first blood stream tree 611 among a plurality of blood stream trees displayed on a 3D ultrasound rendering image 610. Upon receiving the user input for selecting the first blood stream tree 611, the image processor 210 (see FIG. 2) may select only a first blood stream tree 601 among the plurality of blood stream trees included in the 3D ultrasound volume data 600. The first blood stream tree 611 displayed on the display 630 may refer to the same blood stream as the first blood stream tree 601 included in the 3D ultrasound volume data 600.

Referring to FIG. 6B, the display 630 may display a plurality of blood stream trees on the 3D ultrasound rendering image 610 of a target object, and the ultrasound imaging apparatus may receive a user input for selecting a second blood stream tree 612 of the plurality of blood stream trees. Upon receiving the user input for selecting the second blood stream tree 612, the image processor 210 (see FIG. 2) may select only the second blood stream tree 612 among the plurality of blood stream trees included in the 3D ultrasound volume data 600. The second blood stream tree 612 displayed on the display 630 may include the same blood stream as a second blood stream tree 602 included in the 3D ultrasound volume data 600.

Referring to FIG. 6C, the ultrasound imaging apparatus may receive a user input for connecting the first blood stream tree 611 and the second blood stream tree 612. Referring to 6A and 6B, the first blood stream tree 601 and the second blood stream tree 602 may be split blood stream trees that are not classified into one blood stream tree through a pre-processing process and a blood stream boundary detection process in the 3D ultrasound volume data 600. Upon receiving the user input for connecting the first blood stream tree 611 and the second blood stream tree 612, the image processor 210 (see FIG. 2) may simultaneously select the first blood stream tree 601 and the second blood stream tree 602 in the 3D ultrasound volume data 600 and merge the first blood stream tree 601 and the second blood stream tree 602 into a third blood stream tree 603. The display 630 may connect the first blood stream tree 611 and the second blood stream tree 612 and merge and display the first blood stream tree 611 and the second blood stream tree 612 into a third blood stream tree 613.

In an embodiment shown in FIGS. 6A to 6C, when a user wishes to simultaneously observe blood streams split from each other, the ultrasound imaging apparatus may receive a user input for selecting each of the first blood stream tree 611 and the second blood stream tree 612 displayed on the 3D ultrasound rendering image 610, and display only the selected first blood stream tree 611 and second blood stream tree 612. At least two blood stream trees to be observed by the user may be simultaneously displayed, and thus blood stream visibility and user convenience may be improved.

Although not shown in FIGS. 6A to 6C, in an embodiment of the disclosure, the ultrasound imaging apparatus may receive a user input for separating a blood stream tree classified into one blood stream tree into at least two blood streams. Upon receiving the user input for separating one blood stream tree into the at least two blood streams, the ultrasound imaging apparatus may split the selected blood stream tree into the at least two blood streams and display only selected blood stream among the split blood streams. In another embodiment, the ultrasound imaging apparatus may receive a user input for removing any of the split blood streams.

Figure 7:
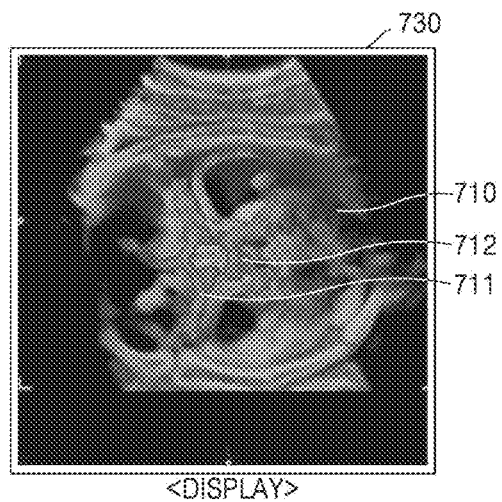
FIG. 7 is a diagram for explaining a method, performed by an ultrasound imaging apparatus, of displaying a blood stream of interest in an ultrasound image, according to an embodiment of the disclosure.

FIG. 7 is a diagram for explaining a method, performed by an ultrasound imaging apparatus, of displaying a blood stream of interest in an ultrasound image on a display 730 according to an embodiment of the disclosure.

Referring to FIG. 7, the ultrasound imaging apparatus may receive a user input for mapping different colors to a first blood stream 711 and a second blood stream 712 displayed on a 3D ultrasound rendering image 710. In an embodiment, the first blood stream 711 may be arterial blood, and the second blood stream 712 may be venous blood. In an embodiment, the ultrasound imaging apparatus may receive a user input for mapping a red color to the blood first blood stream 711 that is the arterial blood, and a blue color to the second blood stream 712 that is the venous blood. However, this is an example, and types of the first blood stream 711 and the second blood stream 712, and the colors mapped thereto are not limited to the above examples.

The ultrasound imaging apparatus may assign the mapped colors to the first blood stream 711 and the second blood stream 712 based on the user input. The display 730 may display the colors assigned to the first blood stream 711 and the second blood stream 712 on the 3D ultrasound rendering image 710.

In a two-dimensional (2D) ultrasound image or the like, a color of a blood stream may be determined based on a location of a probe. For example, when a movement direction of the blood stream is closer toward the probe, the blood stream may be displayed in a red color, and when the movement direction of the blood stream is away from the probe, the blood stream may be displayed in a blue color. However, since the 3D ultrasound rendering image 710 may rotate in 3D, a color display according to the location of the probe and the movement direction of the blood stream may not be accurate. In the embodiment shown in FIG. 7, the ultrasound imaging apparatus may map different colors to the first blood stream 711 and the second blood stream 712 regardless of the location of the probe, based on the user input, and display the mapped colors, thereby improving visibility of the blood stream to be observed by a user.

Figure 8:
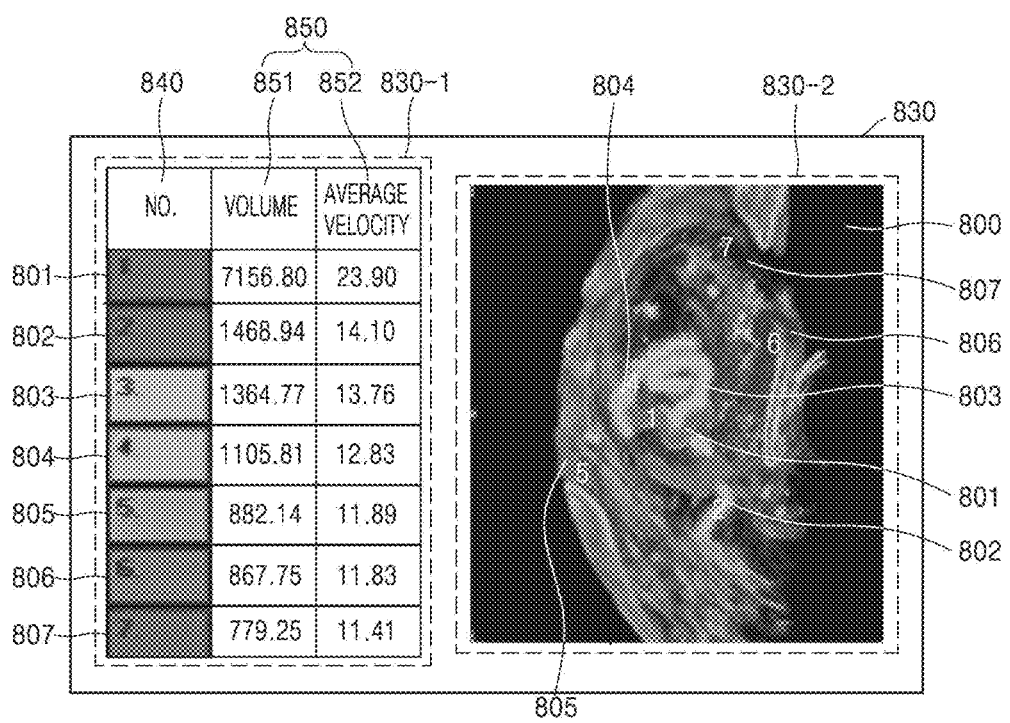
FIG. 8 is a diagram for explaining a method of displaying, on a display of an ultrasound imaging apparatus, a user interface (UI) including ultrasound volume data and a blood stream list in the ultrasound volume data, according to an embodiment of the disclosure.

FIG. 8 is a diagram for explaining a method, a display 830 of an ultrasound imaging apparatus, of displaying a user interface (UI) including an ultrasound image and a blood stream list 840 in the ultrasound image according to an embodiment of the disclosure.

Referring to FIG. 8, the display 830 may display the UI including the list 840 of a plurality of blood stream trees 801 to 807 and blood stream data 850 on a first region 830-1 and display a 3D ultrasound rendering image 800 of a target object on a second region 830-2. The blood stream data 850 may include volume magnitude and average velocity of the blood stream of each of the plurality of blood stream trees 801 to 807 in the target object.

The plurality of blood stream trees 801 to 807 included in the list 840 may be displayed in different colors. For example, the first blood stream tree 801 may be displayed in a red color, the second blood stream tree 802 may be displayed in a blue color, the third blood stream tree 803 may be displayed in a yellow color, the fourth blood stream tree 804 may be displayed in a violet color, the fifth blood stream tree 805 may be displayed in a orange color, the sixth blood stream tree 806 may be displayed in a cyan color, and the seventh blood stream tree 807 may be displayed in a purple color. However, this is an example, and the color of each blood stream tree is not limited to the above example.

In an embodiment, the colors of the first blood stream tree 801 to the seventh blood stream tree 807 may be predetermined colors, but are not limited thereto, and may be randomly determined.

The plurality of blood stream trees 801 to 807 may be displayed on the 3D ultrasound rendering image 800 of the target object in the second region 830-2 of the display 830 in the same colors as the colors displayed on the list 840.

The ultrasound imaging apparatus may receive a user input for selecting any one of the plurality of blood stream trees 801 to 807 included in the list 840 displayed on the first region 830-1 of the display 830. In an embodiment, upon receiving a user input for selecting the first blood stream tree 801 among the plurality of blood stream trees 801 through 807 displayed on the list 840, the display 830 may visualize and display only the first blood stream tree 801 among the plurality of blood stream trees 801 to 807. That is, the second blood stream tree 802 through the seventh blood stream tree 807 excluding the first blood stream tree 801 among the plurality of blood stream trees 801 through 807 may not be displayed.

In the embodiment shown in FIG. 8, the ultrasound imaging apparatus may display the UI including the list 840 of the plurality of blood stream trees 801 through 807 included in the target object, and receive a user input for selecting a blood stream tree including a blood stream of interest through the UI, thereby improving user convenience.

Figure 9:
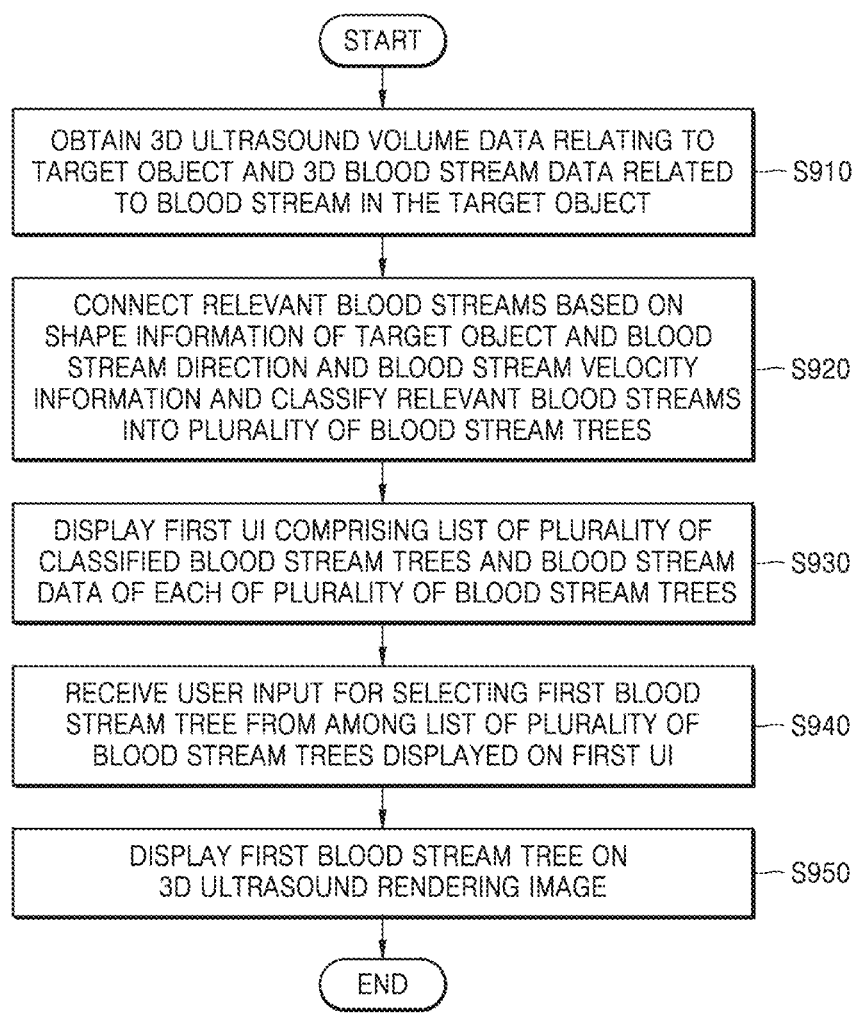
FIG. 9 is a flowchart illustrating a method of displaying, by an ultrasound imaging apparatus, a blood stream of interest included in an ultrasound rendering image of a target object, according to an embodiment of the disclosure.

FIG. 9 is a flowchart illustrating a method of displaying, by an ultrasound imaging apparatus, a blood stream of interest included in an ultrasound image of a target object according to an embodiment of the disclosure.

In operation S910, the ultrasound imaging apparatus obtains 3D ultrasound volume data of the target object and 3D blood stream data of a blood stream. In operation S920, the ultrasound imaging apparatus connects and classifies relevant blood streams based on shape information of the target object and information of a blood stream movement direction and a blood stream velocity into a plurality of blood stream trees. Operations S910 and S920 are the same as operations S310 and S320 described in FIG. 3, and thus redundant descriptions thereof are omitted.

In operation S930, the ultrasound imaging apparatus displays a first UI including a list of the plurality of classified blood stream trees and blood stream data of each of the plurality of blood stream trees. In an embodiment, the ultrasound imaging apparatus may display the first UI along with a 3D ultrasound rendering image of the target object. In an embodiment, the first UI may include the list that displays the plurality of blood stream trees in different colors. In an embodiment, the blood stream data included in the first UI may include information about volume magnitude of each of the plurality of blood stream trees and a blood stream average velocity.

In operation S940, the ultrasound imaging apparatus receives a user input for selecting a first blood stream tree among the list of the plurality of blood stream trees displayed on the first UI. In an embodiment, the ultrasound imaging apparatus may receive a mouse click input for clicking a UI displaying the first blood stream tree among the plurality of blood stream lists, or a touch input for touching a UI displaying the first blood stream tree, but is not limited thereto.

In operation S950, the ultrasound imaging apparatus displays the first blood stream tree on the 3D rendering image. In an embodiment, the ultrasound imaging apparatus may visualize and display only the first blood stream tree on the 3D rendering image, and may not display the remaining blood stream trees except for the first blood stream tree among the plurality of blood stream trees.

Figure 10:
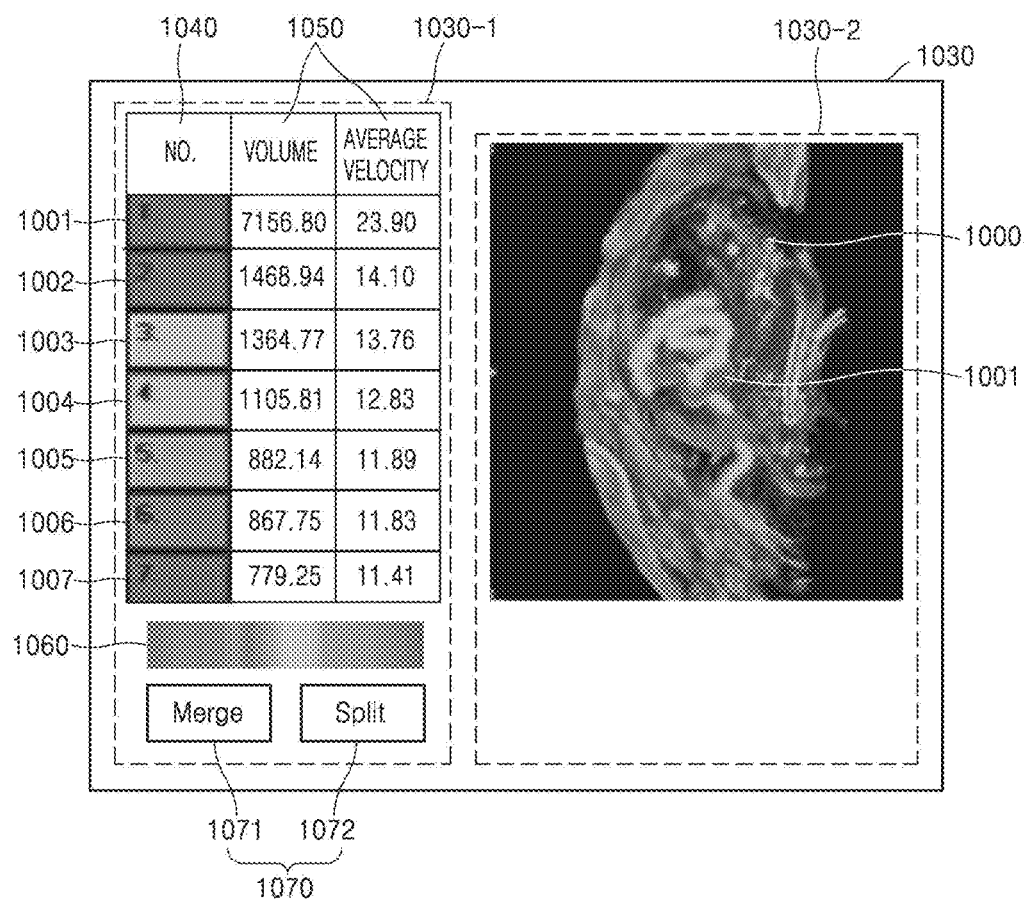
FIG. 10 is a diagram for explaining a method of displaying, on a display of an ultrasound imaging apparatus, a UI including ultrasound volume data, a blood stream list in the ultrasound volume data, and a button-type interface, according to an embodiment of the disclosure.

FIG. 10 is a diagram for explaining a method, performed by a display 1030 of an ultrasound imaging apparatus, of displaying a UI including an ultrasound image, a blood stream list 1040 in the ultrasound image and a button-type interface according to an embodiment of the disclosure.

Referring to FIG. 10, the display 1030 may display a first UI including the blood stream tree list 1040 and blood stream data 1050, a second UI 1060 receiving a user input for mapping a color to a blood stream tree and a third UI 1070 receiving a user input for connecting or disconnecting blood stream trees on a first region 1030-1. The display 1030 may display a 3D ultrasound rendering image 1000 of a target object on a second region 1030-2. The blood stream tree list 1040 and the blood stream data 1050 of the first UI are the same as the list 840 and the blood stream data 850 described in FIG. 8, respectively, and thus redundant descriptions thereof are omitted.

The second user interface 1060 may receive a user input for mapping a color to each of a plurality of blood stream trees 1001 through 1007 displayed on the blood stream tree list 1040. The second UI 1060 may display a plurality of colors, and may receive a user input for selecting any of the plurality of colors and mapping the selected color to a specific blood stream tree. For example, the ultrasound imaging apparatus may receive a first user input for selecting the first blood stream tree 1001 displayed in a red color through the blood stream tree list 1040, and may receive a second user input for selecting a blue color through the second UI 1060. The ultrasound imaging apparatus may map the blue color to the first blood stream tree 1001 based on the received first user input and second user input.

The display 1030 may display the first blood stream tree 1001 on the second region 1030-2 in the selected blue color based on the user input.

The third UI 1070 may include a first button interface 1071 receiving a user input for connecting at least two blood stream trees among the plurality of blood stream trees 1001 to 1007 included in the blood stream tree list 1040, and a second button interface 1072 receiving a user input for separating the selected blood stream tree into at least two blood stream trees. The first button interface 1071 may be, for example, a merge interface selecting the first blood stream tree 1001 and the second blood stream tree 1002 and connecting the first blood stream tree 1001 and the second blood stream tree 1002 as one blood stream tree. The second button interface 1072 may be, for example, a split interface receiving a user input for splitting the first blood stream tree 1001 into at least two blood stream trees or at least two blood streams.

The second user interface 1060 and the third user interface 1070 may include the button-type interface. In an embodiment, the second user interface 1060 and the third user interface 1070 may be configured as a GUI. In an embodiment, the display 1030 may be configured as a touch screen, and may receive a user touch input through the second user interface 1060 and the third user interface 1070.

In the embodiment shown in FIG. 10, the ultrasound imaging apparatus may display the second user interface 1060 receiving the user input for mapping a color to a blood stream and the third user interface 1070 receiving the user input for connecting or splitting the blood streams as well as the blood stream tree list 1040, thereby improving intuitiveness, efficiency, and convenience of use.

Figure 11:
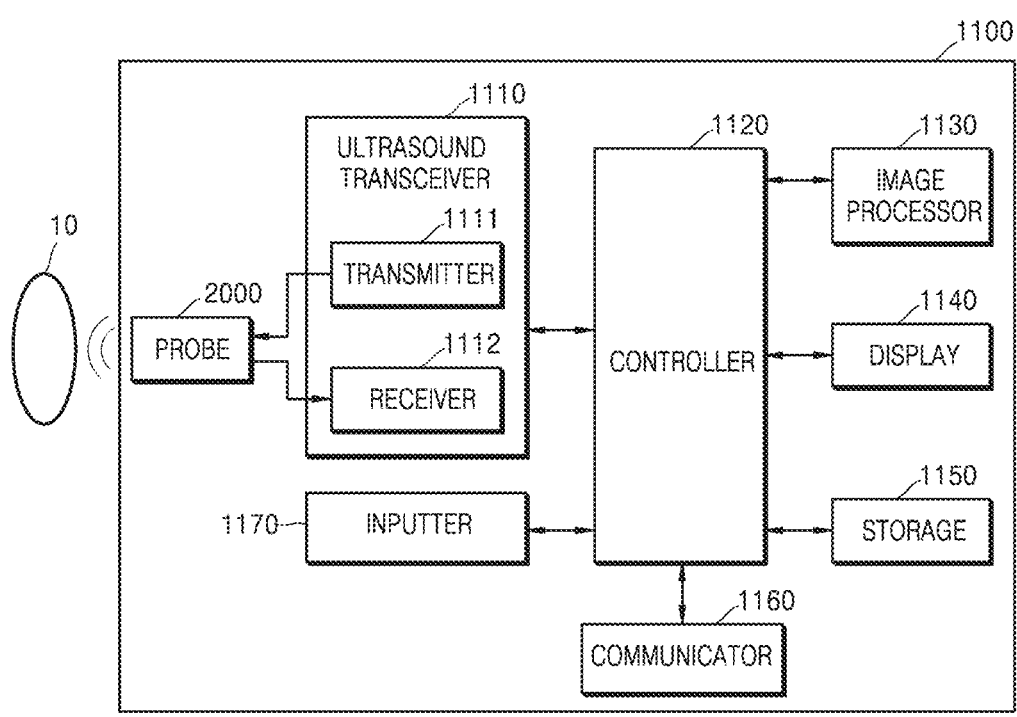
FIG. 11 is a block diagram showing a structure of an ultrasound imaging apparatus according to an embodiment of the disclosure.

FIG. 11 is a block diagram showing a structure of an ultrasound imaging apparatus 1100 according to an embodiment of the disclosure. The ultrasound imaging apparatus 1100 according to an embodiment may include a probe 2000, an ultrasound transceiver 1110, a controller 1120, an image processor 1130, a display 1140, a storage 1150, a communicator 1160, and an inputter 1170.

The ultrasound imaging apparatus 1100 may be configured not only as a cart type but also as a portable type. Examples of the portable ultrasound imaging apparatus 1100 include, but are not limited to, a smart phone including a probe and an application, a laptop computer, a PDA, a tablet PC, and the like.

The probe 2000 may include a plurality of transducers. The plurality of transducers may transmit ultrasound signals to the object 10 according to a transmission signal applied from a transmitter 1111. The plurality of transducers may receive the ultrasound signals reflected from the object 10 and form a received signal. Also, the probe 2000 may be implemented integrally with the ultrasound imaging apparatus 1100 or may be implemented as a separate type connected to the ultrasound imaging apparatus 1100 by wired or wirelessly. Also, the ultrasound imaging apparatus 1100 may include one or a plurality of probes 2000 according to an implementation.

The controller 1120 controls the transmitter 1111 to form a transmission signal to be applied to each of the plurality of transducers in consideration of locations and focusing points of the plurality of transducers included in the probe 2000.

The controller 1120 performs analog-to-digital conversion of the received signal received from the probe 2000, and sums the digitally converted received signal in consideration of the locations and focusing points of the plurality of transducers, to control a receiver 1112 to generate ultrasound data.

The image processor 1130 generates an ultrasound image using the ultrasound data generated by the receiver 1112.

The display 1140 may display the generated ultrasound image and various information processed by the ultrasound imaging apparatus 1100. The ultrasound imaging apparatus 1100 may include one or a plurality of displays 1140 according to an implementation. Also, the display 1140 may be implemented as a touch screen in combination with a touch panel.

The controller 1120 may control the overall operation of the ultrasound imaging apparatus 1100 and a signal flow between internal components of the ultrasound imaging apparatus 1100. The controller 1120 may include a memory storing programs or data for performing functions of the ultrasound imaging apparatus 1100, and a processor processing the programs or data. The controller 1120 may also receive a control signal from the inputter 1170 or an external device to control the operation of the ultrasound imaging apparatus 1100.

The ultrasound imaging apparatus 1100 includes the communicator 1160 and may be connected to an external device (for example, a server, a medical device, a portable device (smartphone, tablet PC, wearable device, etc.) through the communicator 1160.

The communicator 1160 may include one or more components that enables communication with an external device, for example, at least one of a short-range communication module, a wired communication module, and a wireless communication module.

The communicator 1160 receives a control signal and data from the external device and transmits the received control signal to the controller 1120 such that the controller 1120 controls the ultrasound imaging apparatus 1100 according to the received control signal.

Alternatively, the controller 1120 may transmit the control signal to the external device through the communicator 1160, thereby controlling the external device according to the control signal of the controller 1120.

For example, the external device may process data of the external device according to the control signal of the controller 1120 received through the communicator 1160.

The external device may be provided with a program for controlling the ultrasound imaging apparatus 1100. The program may include an instruction for performing a part or all of the operation of the controller 1120.

The program may be installed in an external device in advance, or a user of the external device may download and install the program from a server that provides an application. The server providing the application may include a recording medium storing the program.

The storage 1150 may store various data or programs for driving and controlling the ultrasound imaging apparatus 1100, input/output ultrasound data, and obtained ultrasound images, etc.

The inputter 1170 may receive a user input for controlling the ultrasound imaging apparatus 1100. For example, the user input may include an input for operating a button, a keypad, a mouse, a trackball, a jog switch, a knob, etc., an input for touching a touch pad or a touch screen, a voice input, a motion input, a bio information input (e.g., iris recognition, fingerprint recognition, etc.), and the like but is not limited thereto.

An example of the ultrasound imaging apparatus 1100 according to an embodiment will be described later with reference to FIG. 12.

Figure 12C:
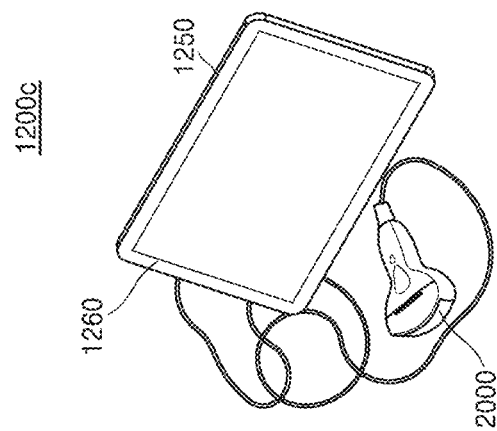
FIG. 12 is a diagram illustrating ultrasound imaging apparatuses according to an embodiment of the disclosure.
Figure 12B:
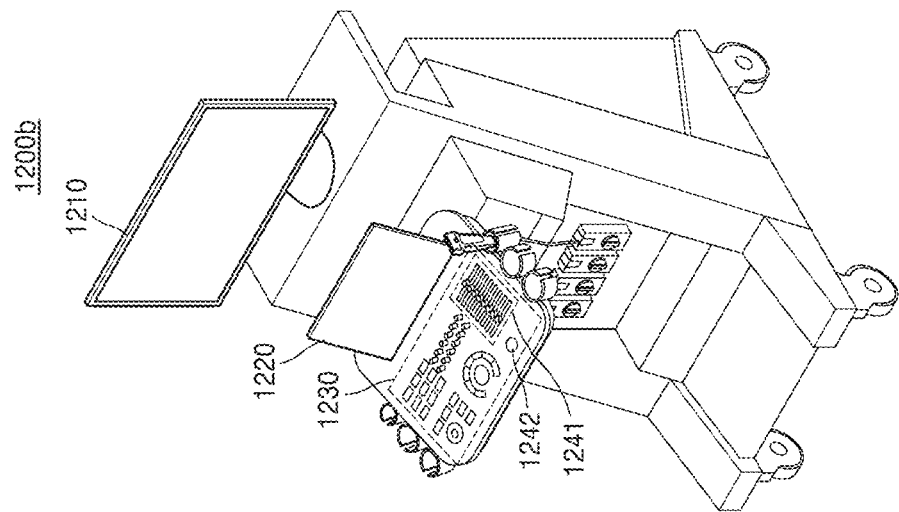
Figure 12A:
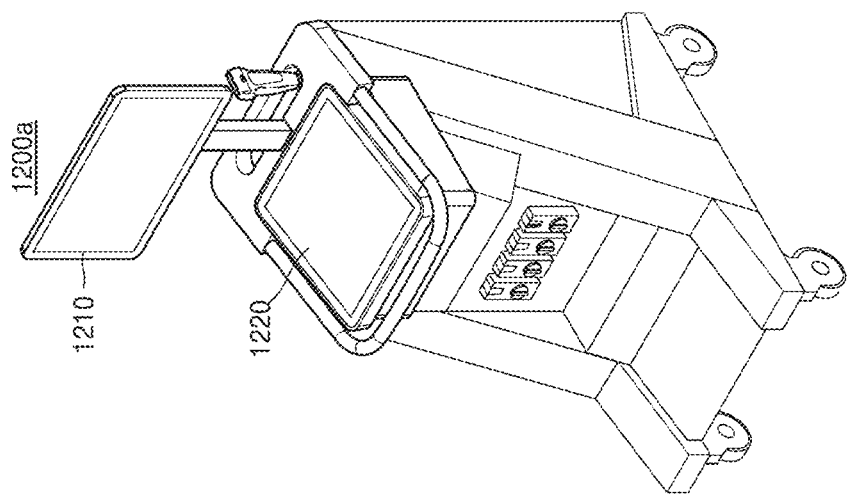

FIG. 12 is a diagram illustrating ultrasound imaging apparatuses 1200a, 1200b, and 1200c according to an embodiment of the disclosure.

Referring to FIG. 12, the ultrasound imaging apparatuses 1200a and 1200b may include a main display 1210 and a sub display 1220. One of the main display 1210 and the sub display 1220 may be implemented as a touch screen. The main display 1210 and the sub display 1220 may display ultrasound images or various information processed by the ultrasound imaging apparatuses 1200a and 1200b. Also, the main display 1210 and the sub display 1220 may be implemented as a touch screen and provide a GUI, thereby receiving data for controlling the ultrasound imaging apparatuses 1200a and 1200b from a user. For example, the main display 1210 may display an ultrasound image, and the sub display 1220 may display a control panel for controlling displaying of the ultrasound image in the form of a GUI. The sub display 1220 may receive data for controlling displaying of an image through the control panel displayed in the form of the GUI. The ultrasound imaging apparatuses 1200a and 1200b may control displaying of the ultrasound images displayed on the main display 1210 using the received control data.

Referring to the ultrasound imaging apparatus 1200b shown in FIG. 12, the ultrasound imaging apparatus 1200b may further include a control panel 1230 in addition to the main display 1210 and the sub display 1220. The control panel 1230 may include a button, a trackball, a jog switch, a knob, and the like, and may receive data for controlling the ultrasound imaging apparatus 1200b from the user. For example, the control panel 1230 may include a Time Gain Compensation (TGC) button 1241, a Freeze button 1242, and the like. The TGC button 1241 is a button for setting a TGC value for each depth of the ultrasound image. Also, when an input of the Freeze button 1242 is detected during the scan of the ultrasound image, the ultrasound imaging apparatus 1200*b* may maintain a state in which a frame image of the point is displayed.

Meanwhile, the button, the trackball, the jog switch, the knob, and the like included in the control panel 1230 may be provided as a GUI on the main display 1210 or the sub display 1220.

Referring to the ultrasound imaging apparatus 1200*c* shown in FIG. 12, the ultrasound imaging apparatus 1200*c* may be implemented in a portable type. Examples of the portable ultrasound imaging apparatus 1200*c* include, but are not limited to, a smart phone including a probe and an application, a laptop computer, a PDA, a tablet PC, and the like.

The ultrasound imaging apparatus 1200*c* includes the probe 2000 and a body 1250. The probe 2000 may be connected to one side of the body 1250 by wired or wirelessly. The body 1250 may include a touch screen 1260. The touch screen 1260 may display an ultrasound image, various information processed by the ultrasound imaging apparatus 1200*c*, a GUI, and the like.

The above-described embodiments of the disclosure may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

While embodiments of the disclosure have been particularly shown and described with reference to the accompanying drawings, it will be understood by those of ordinary skill in the art that various changes in form and details may be made therein without departing from the spirit and scope of the invention as defined by the appended claims. The disclosed embodiments should be considered in descriptive sense only and not for purposes of limitation.

The invention claimed is:

1. An ultrasound imaging apparatus for displaying an ultrasound image of a target object, the ultrasound imaging apparatus comprising:
   an image processor configured to:
   obtain a three-dimensional (3D) ultrasound rendering image relating to the target object and 3D blood stream data related to a blood stream in the target object,
   connect relevant blood streams based on shape information of the target object obtained from the 3D ultrasound rendering image and blood stream direction and blood stream velocity information obtained from the 3D blood stream data, and
   classify the relevant blood streams into a plurality of blood stream trees based on the shape information of the target object and the blood stream direction and blood stream velocity information;
   a user inputter configured to receive at least one user input for selecting a first blood stream tree including a blood stream of interest from among the plurality of blood stream trees; and
   a display configured to display, on the 3D ultrasound rendering image, the first blood stream tree selected based on the user input,
   wherein the user inputter is further configured to select a second blood stream tree and receive a first user input for connecting the second blood stream tree to the previously selected first blood stream tree, and
   wherein the image processor is further configured to merge the first blood stream tree and the second blood stream tree into a third blood stream tree.

2. The ultrasound imaging apparatus of claim 1, wherein the at least one user input includes a second user input, and wherein the user inputter is further configured receive the second user input for splitting the previously selected first blood stream tree into at least two blood streams.

3. The ultrasound imaging apparatus of claim 1,
   wherein the user inputter is further configured to receive a user input for mapping different colors to an artery and a vein in the first blood stream tree, and
   wherein the display is further configured to display on the 3D ultrasound rendering image the colors respectively mapped to the artery and the vein in the first blood stream tree.

4. The ultrasound imaging apparatus of claim 1, wherein the image processor is further configured to calculate a 3D location coordinate value of a point selected by the at least one user input in the 3D ultrasound rendering image, select a first blood stream existing in the calculated 3D location coordinate value, and select the first blood stream tree connected to the first blood stream.

5. The ultrasound imaging apparatus of claim 1, wherein the display is further configured to display a first user interface (UI) comprising a list of the plurality of classified blood stream trees and blood stream data comprising a volume magnitude and a blood stream average velocity of each of the plurality of blood stream trees.

6. The ultrasound imaging apparatus of claim 5, wherein the user inputter is further configured to receive a user input for selecting the first blood stream tree from among the list of the plurality of blood stream trees displayed on the first UI.

7. The ultrasound imaging apparatus of claim 5, wherein the display is further configured to display a second UI comprising at least one of a first button interface receiving a user input for connecting at least two blood stream trees among the plurality of blood stream trees included in the first UI, a second button interface receiving a user input for splitting a blood stream selected from among the plurality of blood stream trees into at least two blood stream trees, and a third button interface receiving a user input for mapping different colors to the plurality of blood stream trees.

8. A method of displaying an ultrasound image of a target object, the method comprising:
   obtaining a three-dimensional (3D) ultrasound rendering image relating to the target object and 3D blood stream data related to a blood stream in the target object;
   connecting relevant blood streams based on shape information of the target object obtained from the 3D ultrasound rendering image and blood stream direction and blood stream velocity information obtained from the 3D blood stream data, and classifying the relevant blood streams into a plurality of blood stream trees based on the shape information of the target object and the blood stream direction and blood stream velocity information;
   receiving at least one user input for selecting a first blood stream tree including a blood stream of interest from among the plurality of blood stream trees; and
   displaying, on the 3D ultrasound rendering image, the first blood stream tree selected based on the user input,
   wherein the receiving of the at least one user input comprises selecting a second blood stream tree and receiving a first user input for connecting the second blood stream tree to the previously selected first blood stream tree; and merging the first blood stream tree and the second blood stream tree into a third blood stream tree.

9. The method of claim 8, wherein the user input includes a second user input, and wherein the receiving of the at least one user input comprises receiving the second user input for splitting the previously selected first blood stream tree into at least two blood streams.

10. The method of claim 8, wherein the receiving of the at least one user input comprises receiving a user input for mapping different colors to an artery and a vein in the first blood stream tree, and wherein the displaying of the first blood stream tree comprises displaying on the 3D ultrasound rendering image the colors respectively mapped to the artery and the vein in the first blood stream tree.

11. The method of claim 8, wherein the receiving of the at least one user input comprises;

calculating a 3D location coordinate value of a point selected by the user input in the 3D ultrasound rendering image;

selecting a first blood stream existing in the calculated 3D location coordinate value; and selecting the first blood stream tree connected to the first blood stream.

12. The method of claim 8, further comprising: after the classifying of the relevant blood streams into the plurality of blood stream trees, displaying a first user interface (UI) comprising a list of the plurality of classified blood stream trees and blood stream data comprising a volume magnitude and a blood stream average velocity of each of the plurality of blood stream trees.

13. The method of claim 12, wherein the receiving of the at least one user input comprises receiving a user input for selecting the first blood stream tree from among the list of the plurality of blood stream trees displayed on the first UI.

14. The method of claim 12, further comprising: displaying a second UI comprising at least one of a first button interface receiving a user input for connecting at least two blood stream trees among the plurality of blood stream trees included in the first UI, a second button interface receiving a user input for splitting a blood stream selected from among the plurality of blood stream trees into at least two blood stream trees, and a third button interface receiving a user input for mapping different colors to the plurality of blood stream trees.

15. A non-transitory computer-readable recording medium having recorded thereon at least one program for performing the method of claim 8.

* * * * *